United States Patent
Cook

(10) Patent No.: US 11,504,112 B1
(45) Date of Patent: Nov. 22, 2022

(54) SPECIALIZED NEEDLE PACKAGING SYSTEM

(71) Applicant: RIVERPOINT MEDICAL, LLC, Portland, OR (US)

(72) Inventor: Nathan Daniel Cook, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 381 days.

(21) Appl. No.: 16/866,924

(22) Filed: May 5, 2020

(51) Int. Cl.
*A61B 17/06* (2006.01)
*A61B 17/00* (2006.01)
*A61L 2/20* (2006.01)
*A61L 2/26* (2006.01)

(52) U.S. Cl.
CPC .... *A61B 17/06138* (2013.01); *A61B 17/0057* (2013.01); *A61L 2/20* (2013.01); *A61L 2/26* (2013.01); *A61B 2017/00526* (2013.01); *A61L 2202/23* (2013.01)

(58) Field of Classification Search
CPC .......... A61B 17/06138; A61B 17/0057; A61B 2017/00526; A61L 2/20; A61L 2/26; A61L 2202/23
See application file for complete search history.

(56) References Cited

U.S. PATENT DOCUMENTS

| | | | |
|---|---|---|---|
| 6,528,277 B1 | 3/2003 | Hendricks et al. | |
| 10,799,311 B2* | 10/2020 | Loui | A61B 50/30 |
| 2001/0006610 A1* | 7/2001 | Miller | A61L 2/28 |
| | | | 422/129 |
| 2014/0353190 A1* | 12/2014 | Okihara | B65B 55/10 |
| | | | 206/370 |

* cited by examiner

*Primary Examiner* — Nicole M Ippolito
(74) *Attorney, Agent, or Firm* — Timothy E. Siegel Patent Law, PLLC; Timothy E. Siegel

(57) ABSTRACT

A needle package having a sealed outer pouch made of a first material, which is permeable to a sterilizing gas but that is impenetrable to microbes and an inner pouch filled with needles, and made of a second material, which is tough and flexible. Also, an intermediate holder, holding the inner pouch, is sealed within the outer pouch, the intermediate holder being made of a third material having greater rigidity than the second material, and defining an interior volume. Further, sterile surgical needles are held within the inner pouch and the intermediate holder constrains the inner pouch to the interior volume, thereby restricting freedom of movement of the needles to reduce needle repositioning during shipment.

18 Claims, 6 Drawing Sheets

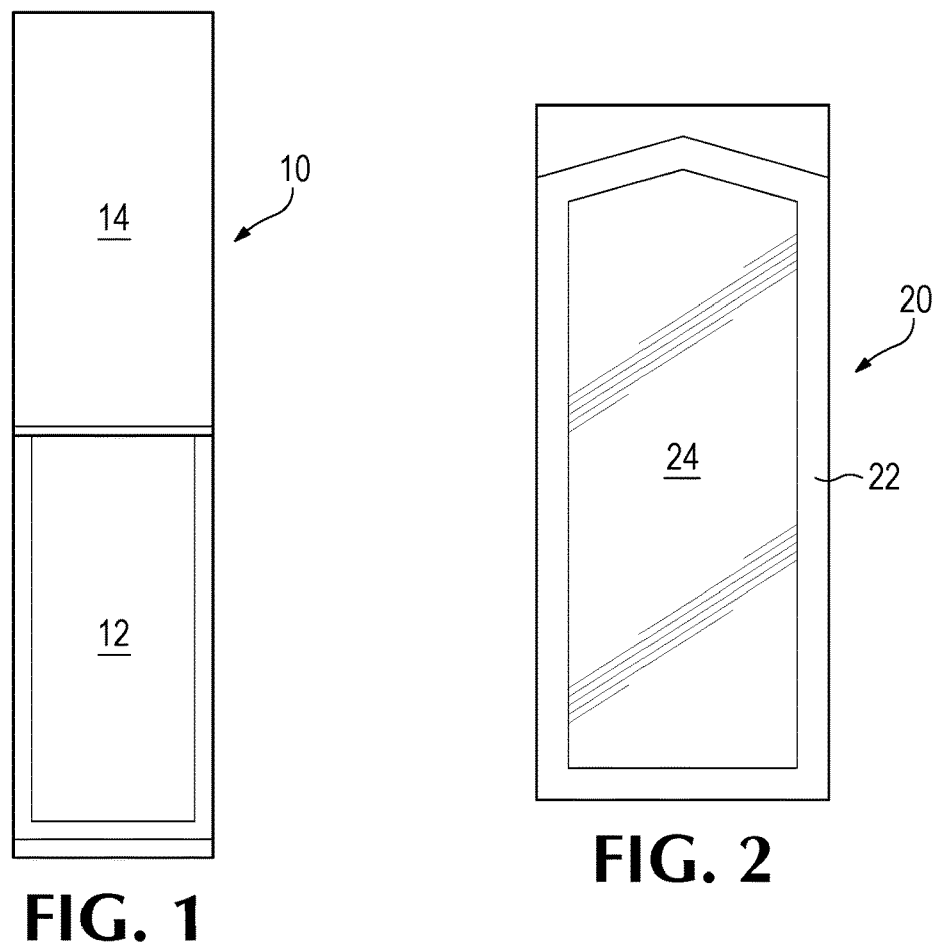
FIG. 1
FIG. 2
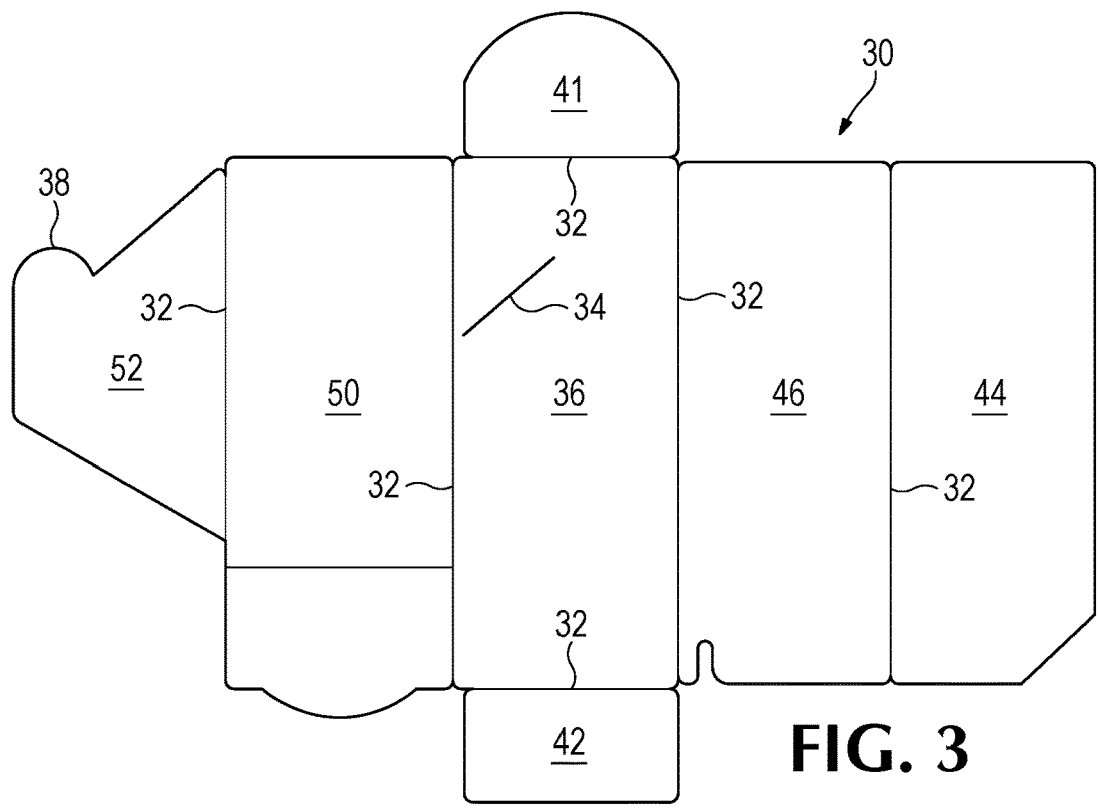
FIG. 3

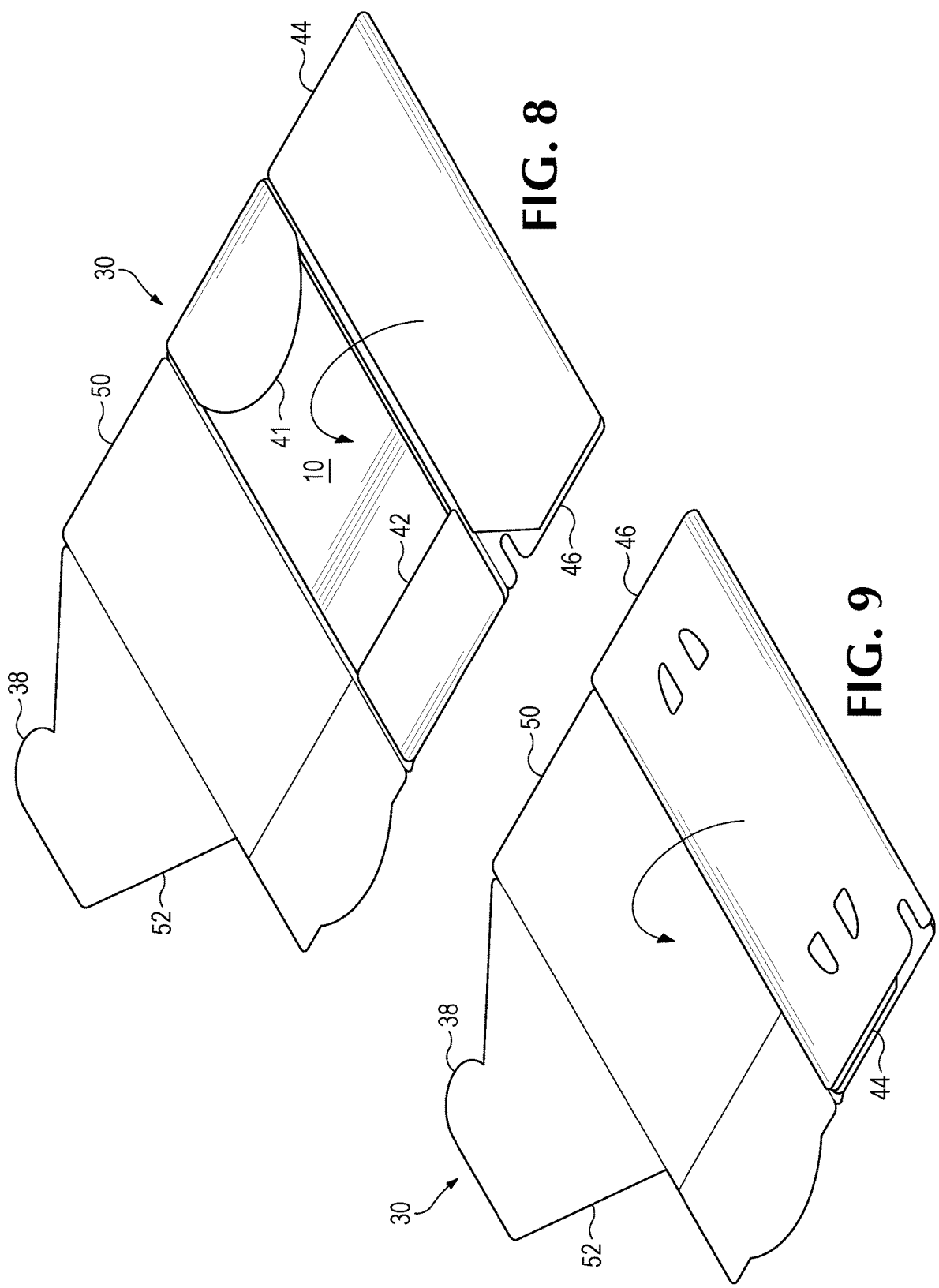

SPECIALIZED NEEDLE PACKAGING SYSTEM

BACKGROUND OF THE INVENTION

A class of specialized needles, that may be used in the production of bioprosthetic heart valves, have very sharp points, creating potential problems in shipment. Because these needles are used in great quantity in the manufacturing process, it is advantageous to send them in packages of more than one hundred. Also, it is a great advantage to deliver these needles to the user in sterile condition, undamaged in the shipping process and neatly arranged, side-by-side. Unfortunately, there appears to be no material that satisfies all of these requirements. Flashspun high-density polyethylene is tough and resistant to being punctured by a needle, but it is flexible, and would let the needles get jumbled in transport. Although the solution of fixing the needles, by for example holding them in an immobile position on a cardboard fixture, as is frequently done in the retail sale of sewing needles, works well for a small number of needles, this is not a practical solution for a container of hundreds of needles.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first, separate aspect, the present invention may take the form of a needle package having a sealed outer pouch made of a first material, which is permeable to a sterilizing gas but that is impenetrable to microbes and an inner pouch filled with needles, and made of a second material, which is tough and flexible. Also, an intermediate holder, holding the inner pouch, is sealed within the outer pouch, the intermediate holder being made of a third material having greater rigidity than the second material, and defining an interior volume. Further, sterile surgical needles are held within the inner pouch and the intermediate holder constrains the inner pouch to the interior volume, thereby restricting freedom of movement of the needles to reduce needle repositioning during shipment.

In a second, separate aspect, the present invention may take the form of a method of packaging specialized needles, that utilizes an inner pouch, made of a flexible, tough material and includes filling the inner pouch with needles. Then, a synthetic paper card, cut in a pattern and scored in a pattern is folded up along the score lines and about the inner pouch, to create a combined inner package. Then, the combined inner package is placed into an outer pouch, made of flexible, tough material, that is permeable to a sterilizing gas, and sealing the outer pouch, to create an unsterilized package. Finally, the unsterilized package is exposed to the sterilizing gas, thereby creating a final sterilized package.

In a third, separate aspect, the present invention may take the form of a method of fabricating a bioprosthetic heart valve that utilizes sterilized needles, packaged in a sealed outer pouch made of a first material, which is permeable to a sterilizing gas but that is impenetrable to microbes and an inner pouch filled with the needles, and made of a second material, which is tough and flexible. An intermediate holder holds the inner pouch, and is sealed within the outer pouch, the intermediate holder being made of a third material having greater rigidity than the second material and defining an interior volume. In the method the outer pouch is cut open, the intermediate holder is opened, and the inner pouch is opened. Then, the needles are kept in the inner pouch, within the intermediate holder, and a fresh needle is taken when needed, threaded with a length of suture and used to sew elements of the bioprosthetic heart valve.

BRIEF DESCRIPTION OF DRAWINGS

Various embodiments of the invention are disclosed in the following detailed description and accompanying drawings.

FIG. 1 is a plan view of an inner pouch, part of an embodiment of the package and method of the present invention.

FIG. 2 is a plan view of an outer pouch, also part of an embodiment of the package and method of the present invention.

FIG. 3 is a plan view of an intermediate card, also part of an embodiment of the package and method of the present invention.

FIG. 8 an isometric view of the elements of FIG. 6, with an arrow showing a third step in folding the card about the inner pouch.

FIG. 9 is an isometric view of the elements of FIG. 6, with an arrow showing a fourth step in folding the card about the inner pouch.

DETAILED DESCRIPTION AND EMBODIMENTS

Figure 4:
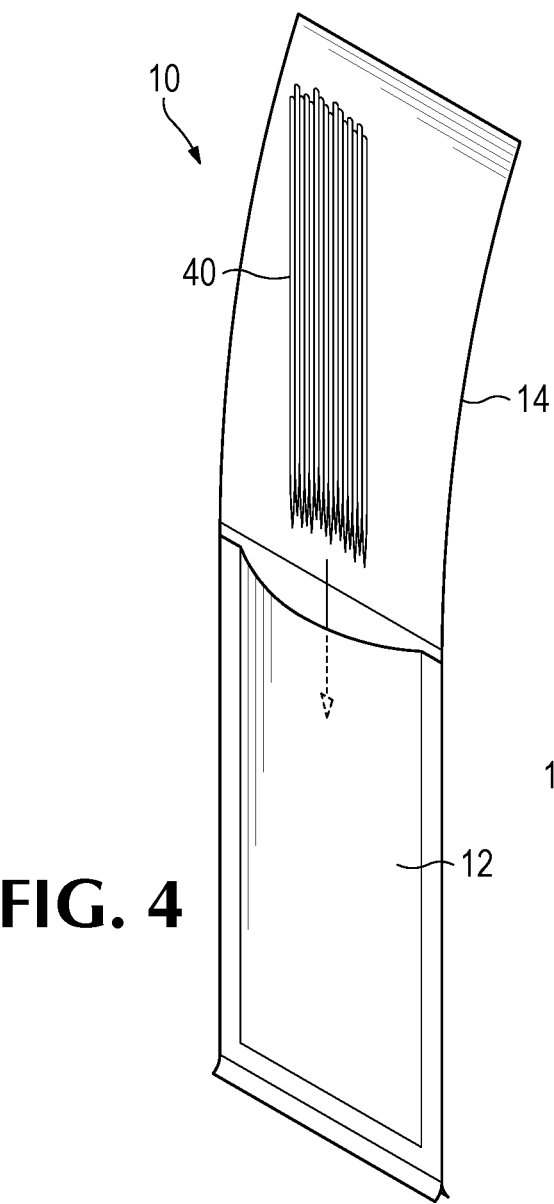
FIG. 4 is an isometric view of the inner pouch of FIG. 1, being filled with needles.

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Flashspun high-density polyethylene (FHDPE) is a flexible tough (difficult to pierce) material, that nevertheless is permeable to ethylene oxide, a sterilizing gas. Because Tyvek® is a popular brand of FHDPE, this class of materials is frequently informally referred to as "Tyvek." The term "tough" as used in this application refers to a material that scores above 4,000 J/m$^2$ in the Spencer puncture test.

Referring to FIG. 1, an inner pouch 10 includes a pocket 12 that is heat sealed on three sides and a flap 14. FIG. 2 shows an outer pouch 20, including a seal zone 22 and a transparent front panel 24. FIG. 3 shows a polylith card 30, that is shaped and scored with lines 32 for a series of folding operations, described below. A slot 34, in a center panel 36 accepts a tab 38 after folding, also described below.

Figure 5:
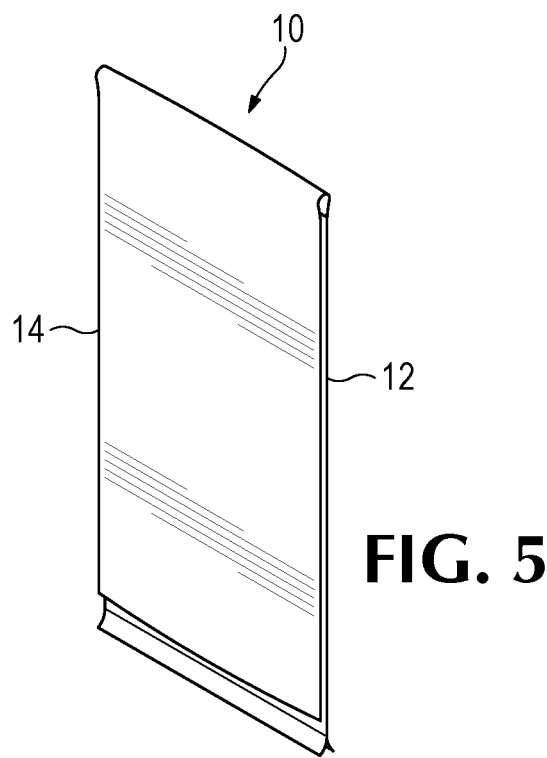
FIG. 5 is an isometric view of the inner pouch of FIG. 1, filled with needles and with the flap folded over.

Referring, now, to FIGS. 4 and 5, needles 40 are placed in pocket 12 of inner pouch 10, and the flap 14 is folded down over the front of pocket 12.

Figure 6:
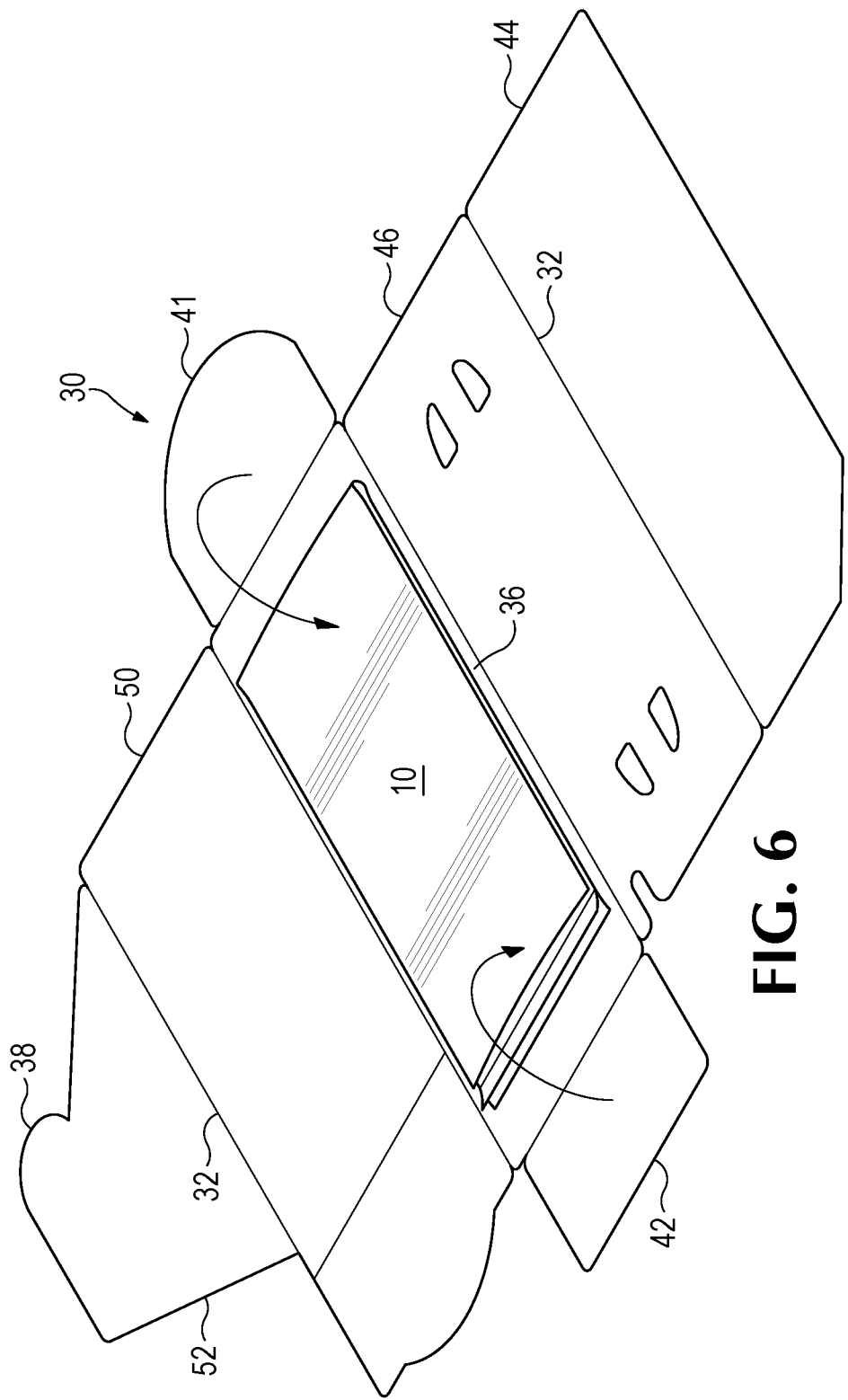
FIG. 6 is an isometric view of the inner pouch of FIG. 5, placed on top of the card of FIG. 3, with arrows illustrating a first step in folding the card about the inner pouch.
Figure 7:
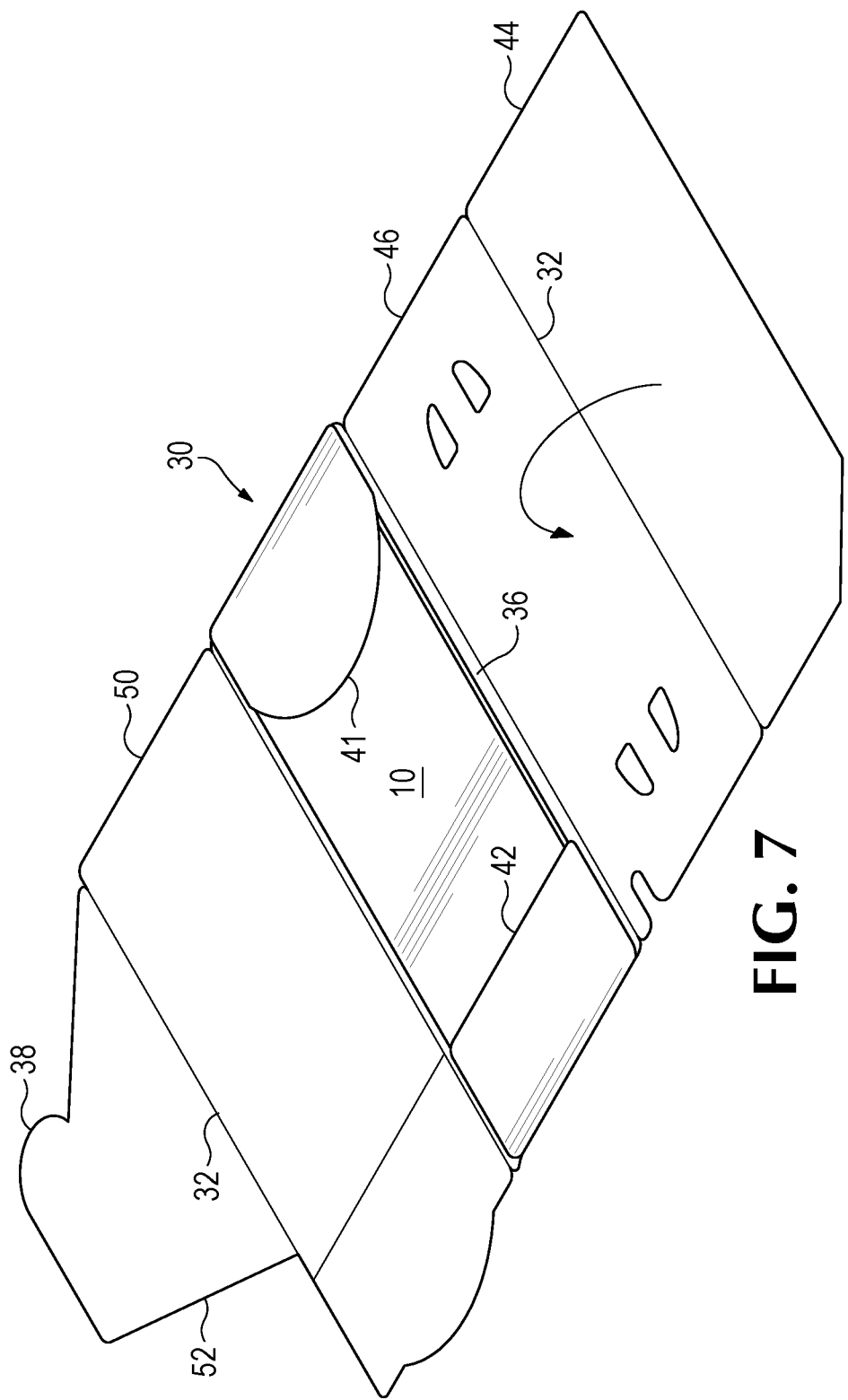
FIG. 7 is an isometric view of the elements of FIG. 6, with an arrow showing a second step in folding the card about the inner pouch.
Figure 10:
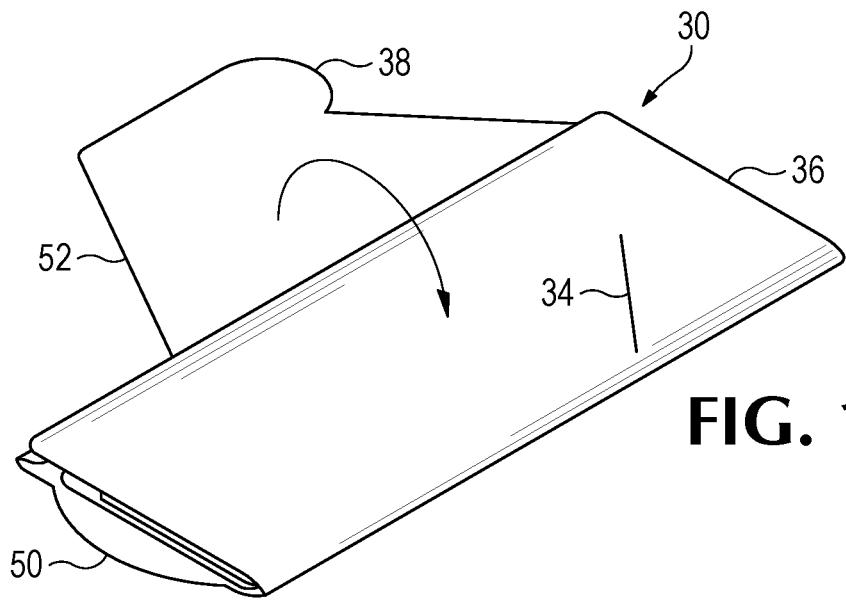
FIG. 10 is an isometric view of the elements of FIG. 6, with an arrow showing a fifth step in folding the card about the inner pouch.
Figure 11:
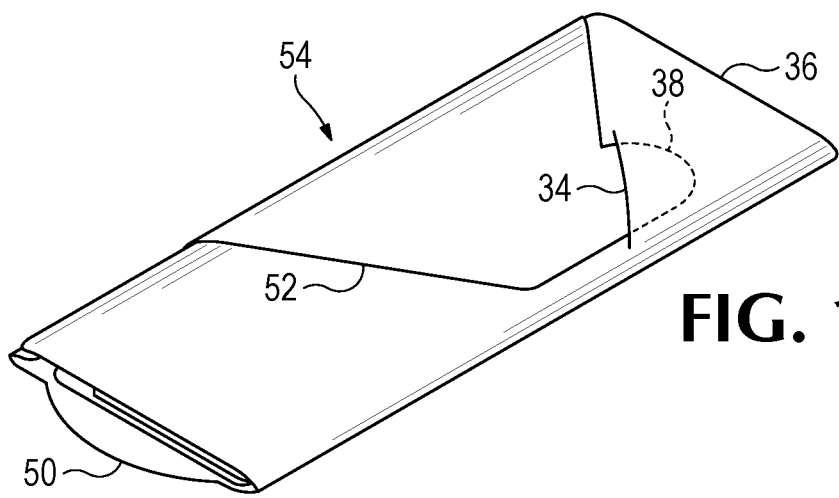
FIG. 11 is an isometric view of the elements of FIG. 6, with an arrow showing a sixth and final step in folding the card about the inner pouch.
Figure 12:
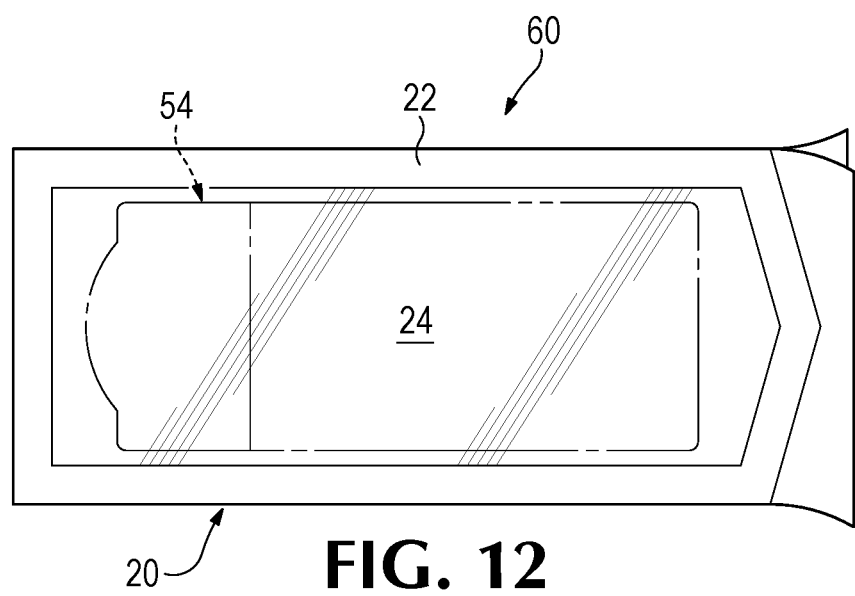
FIG. 12 is a plan view of the final product, with the outer pouch sealed about the inner parts.

Referring to FIG. 6, inner pouch 10 is placed over a center panel of card 30, and a top tab 41 and bottom tab 42 are folded in about inner pouch 10. FIG. 7 shows far right panel 44 being folded in about near right panel 46. FIG. 8 shows both right panels 44 and 46 (now folded together, being folded together over inner pouch 10, which in FIG. 9 (together with both right panels 44 and 46, and center panel 36 is folded over a near left panel 50. In FIG. 10 a far left panel 52 is folded over the combination of panels and inner pouch 10 formed by the previous set of folds, with center panel 36 shown on top, and in FIG. 11, tab 38 is entered into slot 34, to form a finished intermediate holder 54. Finally, as shown in FIG. 12, the holder 54 is placed into and sealed into outer pouch 20, to create a finished package 60, in accordance with the present invention. Finished package 60 is then placed in a chamber of ethylene oxide in sufficient concentration and for a long enough time period to sterilize needles 40. Package 60 has many advantages. Inner pouch 10 prevents the needles from piercing through the polylith intermediate holder. The needles 40 have been sterilized, and the intermediate holder 54, having three panels 36, 44 and 46, and a partial panel 52, folded together about inner pouch 10, has significant protective rigidity to protect needles in shipment, and is also sufficiently rigid to maintain a constricted interior volume, to keep needles 40 in place during shipment. But because the panels have been folded together, there is also some space between neighboring panels, to absorb a blow by yielding slightly, again protecting needles 40.

In embodiments inner pouch 10 is made of tough FHDPE. And outer pouch 20 is formed of FHDPE. Inner pouch 10 must be tough enough to resist being punctured by needles 40, which in one embodiment are particularly sharp, and are about 0.35 mm in diameter at their midpoints.

In a method of use, the needles 40 are used to sew animal tissue to a manmade structure, to produce bioprosthetic heart valves. In differing embodiments between 50 and 1,000 needles are stored in a single package. In one method of use, the needles are kept in the inner portion of package, consisting of inner pouch 10, and intermediate holder 54, after the outer pouch 20 has been opened, and are removed and used as needed. One method of constructing a bioprosthetic heart valve is described in U.S. Pat. No. 10,603,164, which is incorporated herein by reference, as if fully set forth herein. In one embodiment polylith card 30 is made of polylith that is 0.1 mm (4 mils) thick, which is available from Granwell Products, which maintains a website at www.granwell.com. In alternative embodiments, card 30 is between 0.0750 to 0.36 mm thick. In alternative embodiments, card 30 is made of another form of synthetic paper, such as extruded mineral-filled polypropylene paper, mineral-filled polypropylene paper and laminated products. The important quality is that the synthetic paper has a rigidity that is roughly equivalent to the above noted polylith product, and can be die-cut, scored and folded.

In further embodiments, inner pouch 10 is replaced by a multiplicity of sealed pouches, each containing between 1 and 10 sterilized needles, so that the needles can be maintained in sterility until used, or until shortly before use.

The disclosed embodiments are illustrative, not restrictive. While specific configurations of the needle storage and bioprosthetic heart valve production have been described, it is understood that the present invention can be applied to a wide variety of sharps storage and suturing applications. There are many alternative ways of implementing the invention.

What is claimed is:

1. A needle package comprising:
   a) a sealed outer pouch made of a first material, which is permeable to a sterilizing gas but that is impenetrable to microbes;
   b) an inner pouch filled with needles, and made of a second material, which is tough and flexible;
   c) an intermediate holder, holding said inner pouch, and being sealed within said outer pouch, said intermediate holder being made of a third material having greater rigidity than said second material, and defining an interior volume;
   d) sterile surgical needles held within said inner pouch; and
   e) wherein said intermediate holder constrains said inner pouch to said interior volume, thereby restricting freedom of movement of said needles to reduce needle repositioning during shipment.

2. The package of claim 1, wherein said sealed outer pouch is made of flashspun high-density polyethylene (FHDPE).

3. The package of claim 1, wherein said inner pouch is made of FHDPE.

4. The package of claim 1, wherein said intermediate holder is made of polylith.

5. The package of claim 1, wherein said intermediate holder comprises a single piece of said third material that has been folded into form of said intermediate holder.

6. The package of claim 5, wherein said intermediate holder is made of polylith.

7. The package of claim 1, wherein said intermediate holder is made of polylith that is between 0.0750 mm and 0.36 mm thick.

8. A method of packaging specialized needles, comprising:
   a) providing an inner pouch, made of a flexible, tough material;
   b) filling said inner pouch with needles;
   c) providing a synthetic paper card, cut in a pattern and scored in a pattern, and folding up the synthetic paper card, along said score lines and about said inner pouch, to create a combined inner package;
   d) placing said combined inner package into an outer pouch, made of flexible, tough material, that is permeable to a sterilizing gas, and sealing said outer pouch, to create an unsterilized package; and
   e) exposing said unsterilized package to said sterilizing gas, thereby creating a final sterilized package.

9. The package of claim 8, wherein said sealed outer pouch is made of FHDPE.

10. The package of claim 8, wherein said inner pouch is made of FHDPE.

11. The package of claim 8, wherein said intermediate holder is made of polylith.

12. The package of claim 8, wherein said intermediate holder comprises a single piece of said third material that has been folded into form of said intermediate holder.

13. A method of fabricating a bioprosthetic heart valve, comprising:
   a) providing sterilized needles, packaged in:
      i. a sealed outer pouch made of a first material, which is permeable to a sterilizing gas but that is impenetrable to microbes;
      ii. an inner pouch filled with said needles, and made of a second material, which is tough and flexible;
      iii. an intermediate holder, holding said inner pouch, and being sealed within said outer pouch, said intermediate holder being made of a third material having greater rigidity than said second material, and defining an interior volume;
   b) cutting open said outer pouch;
   c) partially unfolding, to open, said intermediate holder;
   d) opening said inner pouch; and
   e) keeping said needles in said inner pouch, within said intermediate holder, taking a fresh needle when needed, threading said fresh needle with a length of suture and using said needle to sew elements of said bioprosthetic heart valve.

14. The method of claim 13, wherein said sealed outer pouch is made of FHDPE.

15. The method of claim 13, wherein said inner pouch is made of FHDPE.

16. The method of claim 13, wherein said intermediate holder is made of polylith.

17. The method of claim 13, wherein said intermediate holder comprises a single piece of said third material that has been folded into form of said intermediate holder.

18. The method of claim 13, wherein said inner pouch is one of a plurality of inner pouches, each holding between 1 and 10 sterilized needles, and wherein an additional inner pouch is opened when needed, thereby supplying sterilized needle(s).

* * * * *